(12) United States Patent
Heuer

(10) Patent No.: US 7,939,113 B2
(45) Date of Patent: May 10, 2011

(54) NUTRITIONAL COMPOSITION FOR FACILITATING MUSCLE PUMPS

(76) Inventor: Marvin A. Heuer, Mississauga (CA)

( * ) Notice: Subject to any disclaimer, the term of this patent is extended or adjusted under 35 U.S.C. 154(b) by 0 days.

(21) Appl. No.: 12/291,478

(22) Filed: Nov. 10, 2008

(65) Prior Publication Data

US 2009/0155379 A1 Jun. 18, 2009

Related U.S. Application Data

(63) Continuation of application No. 11/876,390, filed on Oct. 22, 2007, now abandoned, which is a continuation-in-part of application No. 11/119,168, filed on Apr. 29, 2005, now abandoned.

(60) Provisional application No. 60/567,127, filed on Apr. 30, 2004, provisional application No. 60/613,441, filed on Sep. 24, 2004, provisional application No. 60/658,782, filed on Mar. 3, 2005.

(51) Int. Cl.
*A61K 36/00* (2006.01)

(52) U.S. Cl. .......................................................... 424/725

(58) Field of Classification Search .................. None
See application file for complete search history.

(56) References Cited

U.S. PATENT DOCUMENTS

| | | | |
|---|---|---|---|
| 4,698,360 | A | 10/1987 | Masquelier |
| 5,783,603 | A | 7/1998 | Majeed |
| 6,160,172 | A | 12/2000 | Balasubramanyam et al. |
| 6,203,820 | B1 * | 3/2001 | Vickery ........................ 424/646 |
| 6,383,482 | B1 | 5/2002 | Gorsek |
| 6,384,087 | B1 | 5/2002 | Zemel |
| 6,565,851 | B2 | 5/2003 | Rohdewald et al. |
| 6,638,542 | B2 | 10/2003 | Nieuwenhuizen |
| 2002/0068365 | A1 * | 6/2002 | Kuhrts ........................ 436/501 |
| 2003/0207942 | A1 | 11/2003 | Bhaskaran et al. |
| 2004/0071825 | A1 | 4/2004 | Lockwood |
| 2004/0229953 | A1 | 11/2004 | Gokaraju et al. |

FOREIGN PATENT DOCUMENTS

| | | |
|---|---|---|
| JP | 10-262610 | 10/1998 |
| WO | WO 99/03464 | 1/1999 |
| WO | WO 01/43758 | 6/2001 |
| WO | WO 03/053454 | 7/2003 |
| WO | WO 03088947 A1 * | 10/2003 |

OTHER PUBLICATIONS

Twinlab Amino Fuel. Internet Archive Date: Feb. 8, 2004 [Retrieved from the Internet on: Sep. 25, 2009]. Retrieved from: <http://web.archive.org/web/20040208084503/http://www.bodybuilding.com/store/tl/aminoliq.html>.*
BSN Nitrix. Internet Archive Date: Feb. 10, 2003 [Retrieved from the Internet on: Sep. 25, 2009]. Retrieved from: <http://web.archive.org/web/20030414025024/http://www.bodybuilding.com/store/bsn/nitrix.html>.*
Rasmussen et al. An oral essential amino acid-carbohydrate supplement enhances muscle protein anabolism after resistance exercise. J. Appl. Physiol. 2000; 88: 386-392.
Siejersted et al. Intramuscular pressures for monitoring different tasks and muscle conditions. Adv Exp Med Biol. 1995; 384: 339-350. Abstract.
http://web.archive.org/web/*/http://www.bodybuilding.com/store/thermo/xp.html (Internet Archive Date: Apr. 23, 2004; Retrieved from the Internet on: Sep. 15, 2006).
http://web.arcnive.org/web/*/http://www.bodybuilding.com/store/bsn/nitrix.html (Internet Archive Date: Apr. 14, 2003; Retrieved from the Internet on: Sep. 15, 2006).
http://web.archive.org/web/*/http://www.bodybuilding.com/store/fiz/mid.html (Internet Archive Date: Nov. 7, 2003; Retrieved from the Internet on: Sep. 18, 2008).
http://web.archive.org/web/20030414025024/http://www.bodybuilding.com/store/bsn/nitrix.html (Internet Archive Date: Feb. 10, 2003; Retrieved from the Internet on: Sep. 18, 2008).
http://web.archive.org/web/20020402001829/http://www.bodybuilding.com/store/tl/amino2000.html (Internet Archive Date: Apr. 2, 2002; Retrieved from the Internet on: Sep. 18, 2008).
http://web.archive.org/web/20030210143330/http://www.bodybuilding.com/store/mt/nitrobars.html (Internet Archive Date: Feb. 10, 2003; Retrieved from the Internet on: Sep. 18, 2008).
http://web.archive.org/web/20030802001813/http://www.bodybuilding.com/store/nbol/insu.html (Internet Archive Date: Aug. 2, 2003; Retrieved from the Internet on: Sep. 18, 2008).

* cited by examiner

*Primary Examiner* — Amy L Clark

(57) ABSTRACT

A composition for providing a method for creating and prolonging muscle pumps, providing a transducer effect for nitric oxide, increasing nutrient delivery and promoting increased vascular response in individuals. The composition of the present invention comprises citrulline, aspartic acid and creatine. In addition, the nutritional composition may also comprise L-arginine, and maritime pine (bark) extract. The nutritional composition of the present invention may also further comprise L-leucine and L-valine.

15 Claims, No Drawings

NUTRITIONAL COMPOSITION FOR FACILITATING MUSCLE PUMPS

CROSS-REFERENCE TO RELATED APPLICATIONS

This application is a continuation of applicant's U.S. patent application Ser. No. 11/876,390, filed Oct. 22, 2007 now abandoned, which in turn is a Continuation-in-Part and claims priority to U.S. patent application Ser. No. 11/119,168, filed Apr. 29, 2005, now abandoned, which in turn claims priority to Provisional Patent Application Nos. 60/567,127, filed Apr. 30, 2004, 60/613,441 filed Sep. 24, 2004 and 60/658,782 filed Mar. 3, 2005. The entirety of all these are incorporated herein by reference.

FIELD OF THE INVENTION

The present invention relates to nutritional compositions for facilitating muscle pumps. More specifically, the present invention relates to nutritional compositions which provide for creating and prolonging muscle pumps, providing a transducer effect for nitric oxide, increasing nutrient delivery and promoting increased vascular response, e.g., blood flow and circulation, in an individual, a method for achieving same by consuming the nutritional composition and to a method of manufacturing the nutritional composition.

SUMMARY OF THE INVENTION

The present invention, in accordance with at least one embodiment thereof, provides for a nutritional composition for creating and prolonging muscle pumps, providing a transducer effect for nitric oxide, increasing nutrient delivery and promoting increased vascular response, e.g., blood flow and circulation, in an individual, e.g., a human or animal.

The present invention, in accordance with at least one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual.

Furthermore, the present invention, in accordance with at least one embodiment thereof, provides a method of manufacturing a nutritional composition for creating and prolonging muscle pumps, providing a transducer effect for nitric oxide, increasing nutrient delivery and promoting increased vascular response, e.g., blood flow and circulation, in an individual.

Still further, the present invention, in accordance with at least one embodiment thereof, provides a timed-release delivery system for a nutritional composition, the nutritional composition for creating and prolonging muscle pumps, providing a transducer effect for nitric oxide, increasing nutrient delivery and promoting increased vascular response, e.g., blood flow and circulation, in an individual.

DETAILED DESCRIPTION OF THE INVENTION

Definitions

As used herein, the term "an effective amount" refers to an amount effective for creating and prolonging muscle pumps, providing a transducer effect for nitric oxide, increasing nutrient delivery and promoting increased vascular response, e.g., blood flow and circulation, in an individual when administered over a given time period in accordance with a predetermined dosage regimen, e.g., in accordance with the dosage charts set forth in greater detail below. An effective amount of the nutritional composition is preferably from about 0.1 g to about 20 g of the nutritional composition per serving. More preferably, an effective amount of the composition comprises from about 1 g to about 10 g of the nutritional composition per serving. Most preferably, an effective amount of the composition comprises about 7.5 g of the nutritional composition. In another preferred embodiment of the invention, an effective amount of the composition most preferably comprises about 5.85 g of the nutritional composition.

As used herein, the term "essentially pure" preferably refers to a compound that is greater than about 90% pure. More preferably, the term "essentially pure" refers to a compound that is greater than about 95% pure. Most preferably, the term "essentially pure" refers to a compound that is greater than about 98% pure.

As used herein, the term "enriched" refers to a partially purified extract or composition from which undesirable impurities have been removed. The undesirable impurities may be a single compound or multiple compounds. Preferably, "enriched" refers to a composition in which at least 25% of the undesirable impurities have been removed. More preferably, "enriched" refers to a composition in which at least 50% of the undesirable impurities have been removed. Most preferably, "enriched" refers to a composition in which at least 75% of the undesirable impurities have been removed.

As used herein, the term "muscle pump" refers to the flow of blood through the veins and arteries when muscular contraction compresses the blood veins and arteries, which increases the pressure within the veins and arteries and exerts pressure on the blood, causing it to flow, thereby acting as a pumping mechanism.

As used herein, the term "nutritional supplement" includes dietary supplements, diet supplements, nutritional composition, supplemental compositions and supplemental dietary compositions or those similarly envisioned and termed compositions not belonging to the conventional definition of pharmaceutical interventions as is known in the art. Furthermore, "nutritional supplements" as disclosed herein belong to category of compositions having at least one physiological function when administered to a mammal by conventional routes of administration.

One embodiment of the invention provides for a nutritional composition comprising L-citrulline, creatine, and L-aspartic acid. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition. The present invention, in accordance with one embodiment thereof, provides a timed-release delivery system for the nutritional composition.

For instance, in one such embodiment of the invention there is provided a nutritional composition comprising about 0.010 g of L-citrulline, about 1.50 g of creatine, and about 0.050 g of L-aspartic acid per serving. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition. The present invention, in accordance with one embodiment thereof, provides a timed-release delivery system for the nutritional composition.

A further embodiment of the invention provides for a nutritional composition comprising creatine, L-citrulline, aspartic acid L-arginine, L-arginine alpha-ketoglutarate, and French Maritime Pine bark Extract. The present invention, in accordance with one embodiment thereof, also provides, by the ingestion of the nutritional composition, a method for creating and prolonging intense muscle pumps, providing a transducer effect for nitric oxide, increasing nutrient delivery and promoting increased vascular response, e.g. blood flow and circulation, in an individual. Furthermore, the present invention, in accordance with one embodiment thereof, provides a method of manufacturing such a nutritional composition. Preferably, this embodiment is provided in the dosage form of a drink which may be stored as a powder and reconstituted into a drink at the time of ingestion.

For instance, in one such embodiment of the invention there is provided a nutritional composition comprising about 1.50 g of creatine, about 0.05 g of L-citrulline, about 0.050 g of aspartic acid, about 4.0 g of L-arginine, about 0.10 g of L-arginine alpha-ketoglutarate, and about 0.0020 g of French Maritime Pine bark extract per serving. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition.

An additional embodiment of the invention provides for a nutritional composition comprising creatine, L-citrulline, L-aspartic acid, L-arginine, e.g., L-arginine HCL and/or L-arginine alpha-ketoglutarate, and maritime pine (bark) extract. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition.

For instance, in one such embodiment of the invention there is provided a nutritional composition comprising about 1.5 g of creatine malate, about 0.1 g of L-citrulline, about 0.1 g of L-aspartic acid, about 3.1 g of L-arginine, e.g., about 3.0 g of L-arginine HCL and about 0.1 g of L-arginine alpha-ketoglutarate, and about 2 mg of maritime pine (bark) extract per serving. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition. The present invention, in accordance with one embodiment thereof, provides a timed-release delivery system for the nutritional composition.

In another embodiment of the present invention there is provided for a nutritional composition comprising about 1.5 g of creatine malate, about 0.5 g of L-Citrulline, about 0.05 g of L-aspartic acid about 4.0 g L-arginine, about 0.1 g of L-arginine alpha-ketoglutarate, and about 0.002 g of French maritime pine bark extract per serving. The present invention, in accordance with one embodiment thereof, also provides, by the ingestion of the nutritional composition, a method for creating and prolonging muscle pumps, providing a transducer effect for nitric oxide, increasing nutrient delivery and promoting increased vascular response, e.g., blood flow and circulation, in an individual. Furthermore, the present invention, in accordance with one embodiment thereof, provides a method of manufacturing such a nutritional composition.

While not wishing to be bound by theory it is herein understood by the inventors that the nutritional composition of the present invention increases blood flow to skeletal muscle by exploiting the mechanisms involved in nitric oxide (NO) production and smooth muscle relaxation. It is herein understood that the nutritional composition of the present invention increases the dilation of blood vessels, which increases the delivery of nutrients and oxygen while assisting the removal of waste byproducts of metabolism. Increasing NO production by consumption of the nutritional composition of the invention results in wider blood vessels, which can carry more blood to muscles. The increased flow of blood results in delivery of nutrients, oxygen and hormones needed for growth and repair and helps remove undesirable byproducts of metabolism that fatigue muscles.

Creatine

As used herein, term "creatine" refers to the chemical compound CAS Registry No. 57-00-1, also known as, (a-methyl guanido)acetic acid, N-(aminoiminomethyl)-N-glycine, and methylglycocyamine, and Methylguanidoacetic acid, and N-Methyl-N-guanylglycine, whose chemical structure is shown below. As used herein, "creatine" also includes derivatives of creatine such as esters, and amides, and salts, as well as other derivatives, including derivatives that become active upon metabolism. The chemical structure of creatine is as follows:

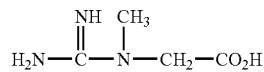

While not wishing to be bound by theory it is herein understood by the inventors that creatine increases strength and muscle size as well as cell volumization.

Creatine and creatine derivatives are widely available from a number of commercial sources. Commercially available creatine derivatives include creatine phosphate, creatine citrate, magnesium creatine, alkaline creatine, creatine pyruvate, creatine hydrates (including, but not limited to creatine monohydrate), creatine taurinate, creatine hydroxycitrate, creatine decanoate, creatine lactate, carnitine creatinate, creatine fumarate, creatine lipoate, creatine arginate, creatine ethyl ester, creatine anhydrous, creatine citrate, encapsulated creatine, effervescent creatine, and creatine malate. Glycocyamine, an in vivo precursor of creatine, is also commercially available and suitable in the practice of the present invention. The supplement preferably comprises creatine malate, dicreatine malate or creatine monohydrate.

As used herein, a serving of the supplement comprises from about 0.1 g to about 10 g of creatine. More preferably, a serving of the supplement comprises from about 0.5 g to about 5 g of creatine. In one embodiment, a serving of the supplement comprises about 1.5 g of creatine. In another embodiment, a serving of the supplement comprises about 0.9 g of creatine.

L-Citrulline

"L-citrulline" is a naturally occurring amino acid, also known as L-N5-(aminocarbonyl)-Ornithine (CAS Registry No. 372-75-8). As used herein, "L-citrulline" also includes derivatives of L-citrulline such as esters, amides, and salts as well as other derivatives, including derivatives that become active upon metabolism. The chemical structure of L-citrulline is as follows:

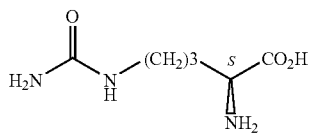

While not being bound by theory, it is herein understood by the inventors that L-citrulline is a metabolic precursor to L-arginine. Thus, L-citrulline increases de novo arginine synthesis thereby increasing the arginine pool. It is hypothesized that ingestion of L-citrulline indirectly supports nitric oxide production by enhancing the plasma concentration of L-arginine substrate for NO synthetase.

As used herein, a serving of the supplement comprises from about 0.01 g to about 10 g of L-citrulline. More preferably, a serving of the supplement comprises from about 0.05 g to about 2 g of L-citrulline. Most preferably, a serving of the supplement comprises about 0.1 g of L-citrulline.

L-Aspartic Acid

"L-aspartic acid" is a naturally occurring amino acid, also known as (S)-Aminobutanedioic acid (CAS Registry No. 5684-8). As used herein, "L-aspartic acid" also includes derivatives of L-aspartic acid such as esters, amides, and salts as well as other derivatives, including derivatives that become active upon metabolism. The chemical structure of L-aspartic acid is as follows:

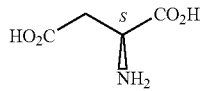

While not being bound by theory it is believed that aspartic acid facilitates the production of nitric oxide.

As used herein, a serving of the supplement comprises from about 0.01 g to about 10 g of L-aspartic acid per serving. More preferably, a serving of the supplement comprises from about 0.02 g to about 2 g of L-aspartic acid per serving. Most preferably, a serving of the supplement comprises about 0.05 g of L-aspartic acid per serving.

L-Arginine

L-arginine, also referred to as (S)-2-Amino-5-[(aminoiminomethyl)amino]pentanoic acid, (CAS Registry No. 74-79-3), is a naturally occurring amino acid. As used herein, the term "L-arginine" also includes derivatives of L-arginine such as esters, and amides, and salts, as well as other derivatives of arginine, including derivatives that become active upon metabolism. The structure of L-arginine is as follows:

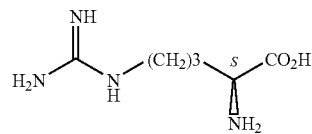

While not being bound by theory it is herein understood that L-arginine is a substrate for NO synthetase and that the ingestion of L-arginine by an animal increases the plasma concentration of L-arginine. It is further believed that increased plasma concentration of L-arginine enhances nitric oxide production by enhancing the concentration of the NO synthetase substrate L-arginine.

The nutritional composition of the invention preferably comprises a salt of L-arginine selected from the group consisting of L-arginine hydrochloride and L-arginine alpha-ketoglutarate. More preferably, the nutritional composition of the invention comprises a combination of salts of L-arginine salts comprising L-arginine hydrochloride and L-arginine alpha-ketoglutarate.

Preferably, the nutritional composition of the invention comprises L-arginine hydrochloride and L-arginine alpha-ketoglutarate in a ratio of at least about 10 to 1. More preferably, the nutritional composition of the invention comprises L-arginine hydrochloride and L-arginine alpha-ketoglutarate in a ratio of at least about 20 to 1. Most preferably, the nutritional composition of the invention comprises L-arginine hydrochloride and L-arginine alpha-ketoglutarate in a ratio of about 30 to 1.

Preferably, a serving of the nutritional substrate comprises from about 1 g to about 30 g of an L-arginine salt per serving. More preferably, a serving of the nutritional substrate comprises from about 5 g to about 10 g of an L-arginine salt per serving. In one embodiment, a serving of the nutritional substrate comprises about 3.0 g to about 3.1 g of an L-arginine salt per serving. In another embodiment, a serving of the nutritional substrate comprises about 1.70 to 1.80 g of an L-arginine salt per serving.

In another preferred embodiment, the nutritional composition of the invention preferably comprises L-arginine base instead of or in addition to an L-arginine salt. Preferably, this nutritional composition of the invention comprises L-arginine and L-arginine alpha-ketoglutarate in a ratio of at least about 10 to 1. More preferably, this nutritional composition of the invention comprises L-arginine and L-arginine alpha-ketoglutarate in a ratio of at least about 20 to 1. Most preferably, this nutritional composition of the invention comprises L-arginine and L-arginine alpha-ketoglutarate in a ratio of about 40 to 1.

Preferably, a serving of this nutritional substrate comprises from about 1 g to about 30 g of L-arginine base per serving. More preferably, a serving of this nutritional substrate comprises from about 5 g to about 10 g of an L-arginine base per serving. In one embodiment, a serving of the nutritional substrate comprises about 4.0 g of an L-arginine base per serving.

The Urea Cycle of the body is capable of using aspartic acid, generally endogenously as a product from the Citric Acids Cycle to ATP-dependently react with citrulline to form argininosuccinate, which is then cleaved to form arginine and fumarate. Arginine is then available to as a substrate from which nitric oxide can be produced. It is herein understood by the inventors that by providing precursors to arginine, such as aspartic acid and citrulline, the body will produce arginine to meet its demands and thus not have a flooded arginine pool. Therefore, in times when creating and prolonging muscle pumps, providing a transducer effect for nitric oxide, increasing nutrient delivery and promoting increased vascular response, e.g., blood flow and circulation, in an individual is required, the body can produce the required arginine.

L-Leucine

"L-leucine" is a naturally occurring amino acid, also known as (S)-2-amino-4-methylpentanoic acid (CAS Registry No. 61-90-5). As used herein, "L-leucine" also includes derivatives of L-leucine such as esters, amides, and salts as well as other derivatives, including derivatives that become active upon metabolism. The chemical structure of L-leucine is as follows:

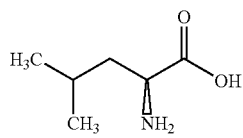

As used herein, a serving of the supplement in one embodiment comprises from about 0.01 g to about 10 g of L-leucine. More preferably, a serving of the supplement comprises from about 0.05 g to about 2 g of L-leucine. In one embodiment, a serving of the supplement comprises about 0.1 g of L-leucine. In another embodiment, a serving of the supplement comprises about 0.06 g of L-leucine.

L-Valine

"L-valine" is a naturally occurring amino acid, also known as (S)-2-amino-3-methylbutanoic acid (CAS Registry No. 72-18-4). As used herein, "L-valine" also includes derivatives of L-valine such as esters, amides, and salts as well as other derivatives, including derivatives that become active upon metabolism. The chemical structure of L-valine is as follows:

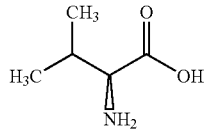

As used herein, a serving of the supplement in one embodiment comprises from about 0.01 g to about 10 g of L-valine. More preferably, a serving of the supplement comprises from about 0.05 g to about 2 g. of L-valine. In one embodiment, a serving of the supplement comprises about 0.1 g of L-valine. In another embodiment, a serving of the supplement comprises about 0.06 g of L-valine.

French Maritime Pine Extract

French Maritime Pine extract preferably refers to an aqueous extract of the bark of the French maritime pine grown as a mono-species forest, spread over the coastal region of south-west France and preferably comprises a natural blend of genetically programmed constant proportions of bioflavonoids including catechin, epicatechin, taxifolin, monomers, dimers of catechin and epicatechin, oligomeric procyanidnins and phenolic fruit acids such as ferulic acid and caffeic acid.

While not being bound by theory it is herein understood by the inventors that the extract from the bark of French maritime pine tree supports circulation by preventing constriction of arteries and blood clotting.

As used herein, a serving of the supplement comprises from about 0.01 mg to about 20 mg of French maritime pine tree bark extract per serving. More preferably, a serving of the supplement comprises from about 0.1 mg to about 10 mg of French maritime pine tree bark extract per serving. Most preferably, a serving of the supplement comprises about 2 mg of French maritime pine tree bark extract per serving.

Those of skill in the art will appreciate that the nutritional composition may contain a variety of excipients.

As set forth above, the present invention, in one embodiment, provides for a method for creating and prolonging muscle pumps, providing a transducer effect for nitric oxide, increasing nutrient delivery and promoting increased vascular response, e.g., blood flow and circulation, in an individual, by consuming a nutritional composition comprising L-citrulline, creatine, and L-aspartic acid. For instance, the present invention, in one embodiment, provides for a nutritional composition comprising about 0.10 g of L-citrulline, about 1.50 g of creatine, and about 0.050 g of L-aspartic acid per serving. Advantageously, the method also includes a workout to facilitate the process of creating and prolonging muscle pumps, providing a transducer effect for nitric oxide, increasing nutrient delivery and promoting increased vascular response, e.g., blood flow and circulation, in an individual. Preferably, the nutritional composition is consumed in accordance with the following directions and dosing chart:

In an alternate embodiment, the present invention provides for a method for creating and prolonging muscle pumps, providing a transducer effect for nitric oxide, increasing nutrient delivery and promoting increased vascular response, e.g., blood flow and circulation, in an individual, by consuming a nutritional composition comprising creatine, L-citrulline, aspartic acid, L-arginine, L-arginine alpha-ketoglutarate and French Maritime Pine bark Extract. For instance, in one embodiment, the present invention provides for a nutritional composition comprising about 1.50 g of creatine, about 0.05 g of L-citrulline, about 0.050 g of aspartic acid, about 4.0 g of L-arginine, about 0.10 g of L-arginine alpha-ketoglutarate, and about 0.0020 g of French Maritime Pine bark extract per serving. Advantageously, the method further comprises a workout to facilitate the process of creating and prolonging muscle pumps, providing a transducer effect for nitric oxide, increasing nutrient delivery and promoting increased vascular response, e.g., blood flow and circulation, in an individual.

Preferably, the nutritional composition is consumed in accordance with the following directions and dosing chart:

DIRECTIONS FOR MEN AND WOMEN: Based upon a person's gender and bodyweight, one serving (2 to 5 caplets) is taken by an individual with an 8 oz. glass of water, 2 times daily. On days of workout, one (1) of these servings is taken by an individual, 30 to 60 minutes before workout.

| Gender/lbs | Minimum daily serving daily serving (caplets) First serving | Second serving | Maximum daily serving daily serving (caplets) First serving | Second serving |
| --- | --- | --- | --- | --- |
| Women < 125 | 2 | 2 | 3 | 3 |
| Women > 125 | 3 | 3 | 4 | 4 |
| Men < 200 lbs | 3 | 3 | 4 | 4 |
| Men > 200 lbs | 4 | 4 | 5 | 5 |

In another example embodiment, the present invention also provides for a method of making a nutritional composition that includes the steps of mixing the following ingredients: creatine, L-aspartic acid, L-citrulline, L-arginine HCL, L-arginine alpha-ketoglutarate, and maritime pine (bark) extract; in addition to the following excipients: potassium chloride, cellulose, dextrose, stearic acid, silica, magnesium stearate, ethyl cellulose, dicalcium phosphate, polyvinyl alcohol, polyethylene glycol, FD&C Red No. 40, talc, and titanium dioxide. The method also includes the step of blending and mixing for 30 minutes. Finally, the method includes the steps of checking for uniformity/homogeneity and then aliquoting into a serving.

The present invention, according to at least one embodiment thereof, may also provide for a timed-release delivery system for a nutritional composition for creating and prolonging muscle pumps, providing a transducer effect for nitric oxide, increasing, nutrient delivery and promoting increased vascular response, e.g., blood flow and circulation, in an individual, which comprises a hydrophilic caplet matrix system comprising water-soluble (i.e., Hydroxypropyl Methyl Cellulose and Hydroxypropylcellulose) and water-insoluble (i.e., Ethyl Cellulose) polymers uniformly incorporated at a specified ratio.

In one timed-release delivery system of the present invention, the nutritional composition includes a hydrophilic caplet matrix system which is in the ratio of 1 Hydroxypropylcellulose:1 Ethyl Cellulose:0.5 Hydroxypropyl Methyl Cellulose.

Although the following examples illustrate the practice of the present invention in some of its embodiments, the examples should not be construed as limiting the scope of the invention. Other embodiments will be apparent to one or ordinary skill in the art from consideration of the specification and examples.

EXAMPLES

Example 1

According to the current embodiment, a serving of the nutritional supplement for creating and prolonging muscle pumps, providing a transducer effect for nitric oxide, increasing nutrient delivery and promoting increased vascular response, e.g., blood flow and circulation, in an individual, includes the following ingredients in tablet form. The current embodiment of the present invention is to be orally administered to an individual.

| Ingredients | 1.60 g/serving | Formula % |
|---|---|---|
| L-citrulline | 0.050 | 3.125% |
| Creatine | 1.500 | 93.75% |
| L-aspartic acid | 0.050 | 3.125% |
| Other Ingredients: | 2.648 g/serving | 35.307% |
| Potassium Chloride | 0.250 | 3.333% |
| Cellulose | 0.883 | 11.773% |
| Dextrose | 0.057 | 0.760% |
| Stearic Acid | 0.560 | 7.467% |
| Silica | 0.070 | 0.933% |
| Magnesium Stearate | 0.035 | 0.467% |
| Ethyl Cellulose | 0.455 | 6.067% |
| Dicalcium Phosphate | 0.338 | 4.507% |
| Total | 7.500 | 100.000% |

Optionally, the caplet form may contain a coating such as Opadry® II.

Example 2

According to the current embodiment, a serving of the nutritional supplement for creating and prolonging muscle pumps, providing a transducer effect for nitric oxide, increasing nutrient delivery and promoting increased vascular response, e.g., blood flow and circulation, in an individual, includes the following ingredients in caplet form. The current embodiment of the present invention is to be orally administered to an individual.

| Ingredients | 5.701 g/serving | Formula % |
|---|---|---|
| L-arginine | 3.999 | 70.146% |
| Creatine | 1.500 | 26.311% |
| L-arginine alpha-ketoglutarate | 0.100 | 1.754% |
| L-citrulline | 0.050 | 0.877% |
| L-aspartic acid | 0.050 | 0.877% |
| French Maritime Pine bark extract | 0.002 | 0.035% |
| Other Ingredients: | 2.800 g/serving | 37.333% |
| Potassium Chloride | 0.250 | 3.333% |
| Cellulose | 1.035 | 13.800% |
| Dextrose | 0.057 | 0.760% |
| Stearic Acid | 0.560 | 7.467% |
| Silica | 0.070 | 0.933% |
| Magnesium Stearate | 0.035 | 0.467% |
| Ethyl Cellulose | 0.455 | 6.067% |
| Dicalcium Phosphate | 0.338 | 4.507% |
| Total | 7.500 | 100.000% |

Optionally, the caplet form may contain a coating such as Opadry® II.

Example 3

A serving of the nutritional composition for creating and prolonging muscle pumps, providing a transducer effect for nitric oxide, increasing nutrient delivery and promoting increased vascular response, e.g., blood flow and circulation, is preferably consumed in accordance with the following directions and dosing chart:

DIRECTIONS FOR MEN AND WOMEN: Based upon a person's gender and bodyweight, one serving (2 to 5 caplets) is taken by an individual with an 8 oz. glass of water, 2 times daily. On days of workout, one (1) of these servings is taken by an individual, 30 to 60 minutes prior to the individual's workout.

| Gender/lbs | Minimum daily serving daily serving (caplets) | | Maximum daily serving daily serving (caplets) | |
|---|---|---|---|---|
| | First serving | Second serving | First serving | Second serving |
| Women < 125 | 2 | 2 | 3 | 3 |
| Women > 125 | 3 | 3 | 4 | 4 |
| Men < 200 | 3 | 3 | 4 | 4 |
| Men > 200 | 4 | 4 | 5 | 5 |

Example 4

A timed-release delivery system for a serving of the nutritional supplement for creating and prolonging muscle pumps, providing a transducer effect for nitric oxide, increasing nutrient delivery and promoting increased vascular response, e.g., blood flow and circulation, in an individual including a hydrophilic caplet matrix of Hydroxypropyl Methyl Cellulose (Methocel K100M Premium CR EP-Hypromellose 2208 USP XXII), Ethyl Cellulose (Ethocel Standard FP Premium—NF XVII), and Hydroxypropylcellulose (Klucel LF—NF XVII) is provided. An experiment to determine the rate of dissolution and thus the release profile of the timed-release delivery system of the present invention was performed. The average (n=6) amount in mg of labeled amount of arginine dissolved from one caplet comprised of the nutritional supplement of the present invention in 900 ml of 0.1N Hydrochloric Acid was recorded in the following table for various time points:

| Time (Minutes) | Average Mg of Arginine Dissolved ± Std. Dev. |
|---|---|
| 15 | 53.02 .±. 8.41 |
| 30 | 105.02 .±. 18.92 |
| 45 | 131.63 .±. 47.6 |
| 60 | 161.9 .±. 27.76 |
| 120 | 284.61 .±. 34.49 |
| 240 | 451.18 .±. 67.49 |
| 360 | 555.59 .±. 157.52 |
| 480 | 590.13 .±. 185.8 |

The preceding data show the timed-release profile for up to 480 minutes following the commencement of dissolution for an embodiment of the present invention.

Example 5

According to the current embodiment, a serving of the nutritional supplement for creating and prolonging muscle pumps, providing a transducer effect for nitric oxide, increasing nutrient delivery and promoting increased vascular response, e.g., blood flow and circulation, in an individual, includes the following ingredients in powder form reconstituted into a drink. The current embodiment of the present invention is to be orally administered to an individual.

| Dietary Ingredient Name | Actives % | Dietary Ingredient per serving (g) | Actives/ serving (g) | Formula % |
|---|---|---|---|---|
| L-arginine | | 4.0000 | | 68.3527% |
| Creatine Malate | | 1.5000 | | 25.6323% |
| Creatine | 63 | | 0.9450 | |
| L-arginine alpha-ketoglutarate (2:1) | | 0.1000 | | 1.7088% |
| Arginine | 69 | | 0.0690 | |
| Picamilone HCL | | 0.1000 | | 1.7088% |
| Asian Ginseng Powder root extract (*Panax ginseng*) | | 0.0500 | | 0.8544% |
| Ginsenosides (standardized) | 25 | | 0.0125 | |
| L-Citrulline | | 0.0500 | | 0.8544% |
| L-aspartic acid | | 0.0500 | | 0.8544% |
| French Maritime Pine Bark Extract (*Pinus Maritima*) | | 0.0020 | | 0.0342% |
| Standardized to Proanthocyanidins | 70 | | 0.0014 | |
| | | 5.8520 | | 100.00% |

| Other Ingredients | g/serving | % |
|---|---|---|
| Dextrose | 6.0000 | 62.9% |
| Citric Acid | 2.4600 | 25.8% |
| SD N&A Bitter Blocker | 0.6250 | 6.5% |
| SD N&A Concord Grape Flavor | 0.1870 | 2.0% |
| Natural Sweetness Modifier Flavor | 0.1750 | 1.8% |
| Sucralose | 0.0550 | 0.6% |
| Acesulfame K | 0.0270 | 0.3% |
| FD&C Blue #1 (10%) | 0.0080 | 0.1% |
| FD&C Red #40 | 0.0060 | 0.1% |
| | 9.5430 | 100.00% |

Example 6

One serving of the supplement of Example 5 is consumed by a human, twice daily.

Example 7

A serving of the nutritional composition for creating and prolonging muscle pumps, providing a transducer effect for nitric oxide, increasing nutrient delivery and promoting increased vascular response, e.g., blood flow and circulation, is according to the present invention administered orally in caplet form to an individual.

| Dietary Ingredient Name | Actives % | Dietary Ingredient per serving (g) | Actives/ serving (g) | Formula % |
|---|---|---|---|---|
| L-arginine | | 4.0000 | | 68.3527% |
| Creatine Malate | | 1.5000 | | 25.6323% |
| Creatine | 63 | | 0.9450 | |
| L-arginine alpha-ketoglutarate (2:1) | | 0.1000 | | 1.7088% |
| Arginine | 69 | | 0.0690 | |
| Picamilone HCL | | 0.1000 | | 1.7088% |
| Asian Ginseng Powder root extract (*Panax ginseng*) | | 0.0500 | | 0.8544% |
| Ginsenosides (standardized) | 25 | | 0.0125 | |
| L-Citrulline | | 0.0500 | | 0.8544% |
| L-aspartic acid | | 0.0500 | | 0.8544% |
| French Maritime Pine Bark Extract (*Pinus Maritima*) | | 0.0020 | | 0.0342% |
| Standardized to Proanthocyanidins | 70 | | 0.0014 | |
| | | 5.8520 | | 100.00% |

Example 8

One serving of the supplement of Example 7 is consumed by a human, twice daily, each serving including 5 caplets as noted according to the dosing regime of Example 3.

Extensions and Alternatives

In the foregoing specification, the invention has been described with a specific embodiment thereof; however, it will be evident that various modifications and changes may be made thereto without departing from the broader spirit and scope of the invention.

What is claimed is:
1. A composition for administration to an individual for enhancing and prolonging muscle pumps, the composition comprising an effective amount of creatine decanoate, L-arginine alpha-ketoglutarate, and L-citrulline.

2. The composition of claim 1, further comprising aspartic acid.

3. The composition of claim 1, further comprising at least one ingredient selected from the group consisting of: creatine malate, creatine citrate, magnesium creatine, alkaline creatine, creatine pyruvate, creatine hydrates, creatine taurinate, creatine hydroxycitrate, creatine lactate, carnitine creatinate, creatine fumarate, creatine lipoate, creatine arginate, creatine ethyl ester, creatine anhydrous, creatine citrate, encapsulated creatine, and effervescent creatine.

4. The composition of claim 3, wherein the at least one ingredient is creatine hydrate in the form of creatine monohydrate.

5. The composition of claim 1, further comprising dicalcium phosphate.

6. The composition of claim 5, further comprising magnesium stearate and stearic acid.

7. The composition of claim 1, further comprising L-leucine and L-valine.

8. The composition of claim 1, further comprising French Maritime Pine bark extract.

9. A composition for administration to an individual for enhancing and prolonging muscle pumps, the composition comprising an effective amount of
   Creatine decanoate;
   L-arginine alpha-ketoglutarate;
   L-citrulline;
   Dicalcium phosphate;
   magnesium stearate; and
   stearic acid.

10. The composition of claim 1, further comprising creatine malate.

11. The composition of claim 1, further comprising creatine fumarate.

12. The composition of claim 1, further comprising creatine lipoate.

13. The composition of claim 1, further comprising creatine lactate.

14. The composition of claim 1, further comprising creatine arginate.

15. The composition of claim 1, further comprising carnitine creatinate.

* * * * *